United States Patent [19]

Schiller

[11] Patent Number: 4,709,384
[45] Date of Patent: Nov. 24, 1987

[54] LAUE CAMERA

[75] Inventor: Claude Schiller, Savigny-sur-Orge, France

[73] Assignee: U.S. Philips Corporation, New York, N.Y.

[21] Appl. No.: 825,845

[22] Filed: Feb. 4, 1986

[30] Foreign Application Priority Data

Feb. 12, 1985 [FR] France ............................. 85 01933

[51] Int. Cl.$^4$ ................. G01N 23/203; G01N 23/207
[52] U.S. Cl. ......................................... 378/76; 378/73
[58] Field of Search ....................... 378/73, 72, 78, 76

[56] References Cited

PUBLICATIONS

Experimental Considerations for Polaroid Film X-ray Photographs, Peters and and Kulin, 8/30/66, The Review of Scientific Instruments, vol. 37, No. 12, Dec. 1966, pp. 1726–1729.

Primary Examiner—Carolyn E. Fields
Assistant Examiner—Joseph A. Hynds
Attorney, Agent, or Firm—Paul R. Miller

[57] ABSTRACT

A Laue camera is provided by incorporating an X-ray source represented by its focus and defined by its two focal dimensions and its exposure angle, a photographic film holder, a collimator taking the form of two diaphragms and placed on the path of the rays between the source and the film, but close to the latter. The X-ray source is used at an exposure angle such that its apparent focal dimensions are of the same size, that the diameter of the openings in the diaphragms is virtually of the same size as the two apparent focal dimensions of the source, that this size is smaller than the average radius desired for a spot in the diffraction diagram obtained from a sample obtained with the aid of this device with the sample being placed close to the surface of the film opposite to the source.

2 Claims, 5 Drawing Figures

LAUE CAMERA

The invention relates to a Laue camera incorporating an X-ray source represented by its focus and defined by its focal dimensions and its exposure angle, a photographic-film holder, a collimator represented by two diaphragms and placed on the path of the rays between the source and the film, but close to the latter.

The invention finds application in the measurement of the orientation of single crystals of new materials and, in particular, of semiconductors in order to form crystals to be used as accretionnuclei or to form substrates intended to receive, for example, epitaxial layers with extreme precision of the orientation being an essential requirement.

A negative-film holder for Laue diagrams is known from U.S. Pat. Nos. 2,495,111, 2,543,160, 2,933,993, 2,483,389, 2,854,909 and the others filed by the Polaroid company between 1949 and 1954. In addition to the properly so-called film holder, this device comprises a collimator formed by a tube with a diaphragm at each extremity, fixed to the holder perpendicularly to the film and a short distance from one of the surfaces of the latter, and a so-called transformation screen fixed to the holder parallel to the film and a short distance from the other face of the latter. This transformation screen transforms X-ray photons into visible photons for more effective use of Polaroid negatives which are not very sensitive to X-rays.

To obtain a Laue diagram with the aid of this device, a beam emerging from an X-ray source is directed towards the collimator, passes through the collimator, the negative film, and then the transformation screen by a circulator hole in the latter, before impinging on the crystal to be studied. The X-ray beam thus forms on the film a spot which constitutes the trace of the direct beam and which delimits the optical axis of the device. The rays reaching the crystal are diffracted by surface crystalline planes and return toward the negative-film holder. On their return path, therefore the diffracted rays impinge on the transformation screen which transforms the X-ray photons into visible photons which, in turn, produce images (spots) on the negative film, thus forming the diffraction diagram of the single crystal. The central spot of this diagram is created by the trace of the direct beam of X-rays.

However, the X-ray sources available on the market have a linear focus which, if this focus line is oriented in such a way that it forms an angle, called the exposure angle, with the optical axis of a device, can be likened, so far as this optical device is concerned, to a more or less point-type source. This source is less punctiform according to whether the exposure angle is greater, which means that the angle at which the extremity of the focus line is viewed is important.

But the Polaroid device described has a collimator whose diaphragm dimensions are large to enable use to be made of commercially available X-ray sources at a large exposure angle, so as to obtain a quantity of radiation which is sufficient to make diffraction diagrams.

This device then produces a spot, due to the transmitted beam, which, on the one hand, is of a large size and, on the other, is surrounded by a halo derived from the rays impinging on the edges of the diaphragm with the result that the localization of the optical axis of the system is extremely inexact.

Furthermore, when the direct beam impinges on the sample to be studied there is, for reflecting crystalline planes which form a given angle with the surface of the sample, diffraction not only of the continuous background emitted by the source corresponding to the full-light spot of the direct beam, but also diffraction of the light originating in the penumbra zone surrounding it. This adds still further to the inaccuracy of measurements which are already rendered difficult by the dimensions of the central spot.

The present invention is aimed at providing a Laue camera which makes it possible to obtain great accuracy as to the orientation of the single crystals by the fact that it permits the realization of diffraction diagrams whose spots are very fine and localized with great precision.

That aim, however, can only be achieved if measures are taken to counteract the trend which consists, so far as the production of X-ray diagrams is concerned, in achieved greater and greater intensity by means of brighter sources and hence of greater exposure angles. For accuracy of measurements a diffraction spot which is not very bright but fine and accurately located has to be aimed for rather a long time than a very bright but large spot, i.e. one obtained on the basis of a diverging incident beam which does not permit precise localization of the spot.

In the present invention the aim for greater accuracy is achieved with a Laue camera of the type described in the preamble, in which the X-ray source is used at an angle of exposure such that its apparent focal dimensions are of the same size, wherein the diameter of the apertures of the diaphragms is of virtually the same size as the apparent focal dimensions of the source with that size being smaller than the mean radius desired for a spot in the diffraction diagram obtained from a crystalline sample with the aid of the Laue camera with this sample being placed close to the film surface opposite to the source.

In one embodiment of the invention, the camera is characterized by the fact that the X-ray source has focal dimensions of $8\times 0.4$ mm and is used at an exposure angle of $3°$, so that its apparent focal dimensions are 0.4 and 0.4 mm, and by the fact that the diameter of the aperture in the diaphragm is also 0.4 mm.

Under these conditions the spot of full light formed by the direct trace of the transmitted beam is very fine and the penumbra zone surrounding it is very greatly decreased. Consequently, the diffraction spots corresponding to the lattice planes of the single crystal to be studied are produced from a very fine incident pencil of rays and are therefore, on the one hand, very fine and, on the other hand, localized in a very precise fashion.

The invention will be more readily understood with the aid of the following description illustrated by the attached figures, of which:

Figure 2:
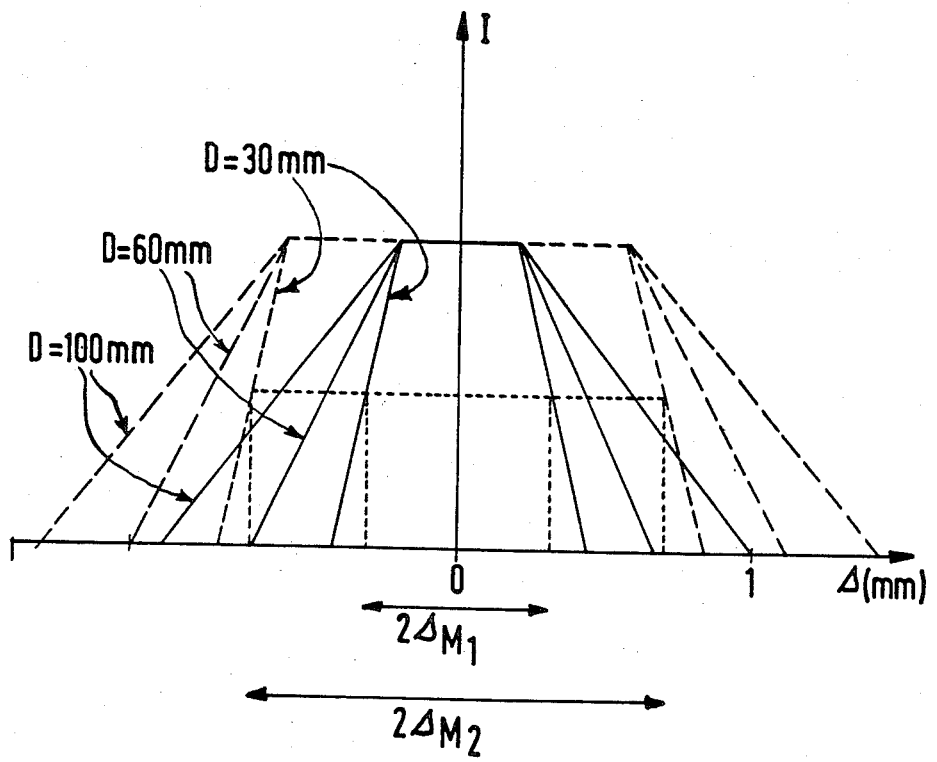
Figure 3A:
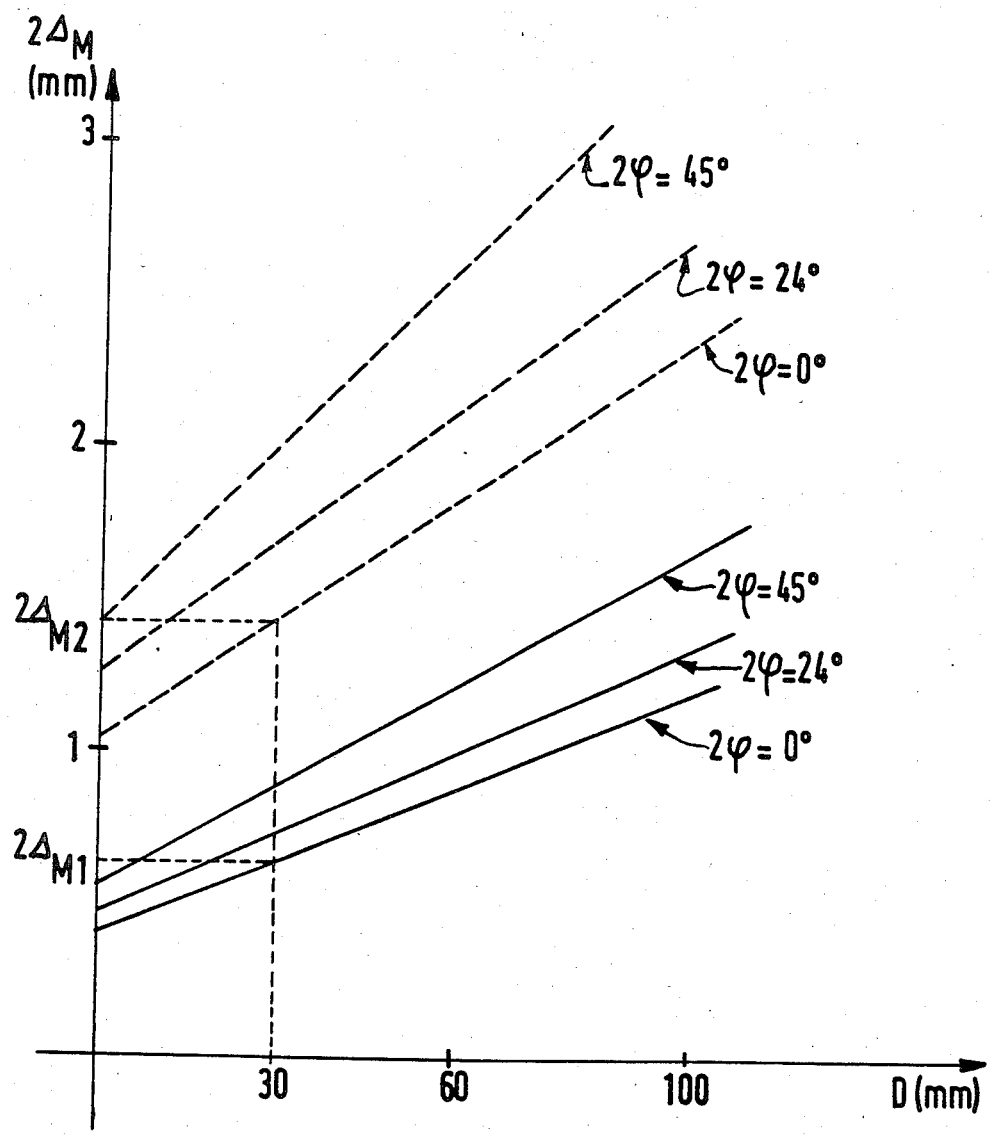

FIG. 2 shows the variation of the brightness of a diffraction spot as a function of the distance $\Delta$ from the center of the spot, where the distance D between the film plane on which the diagram is formed and the sample is taken as a parameter with the continuous-line graph corresponding to an exposure angle $\alpha=3°$, a diffraction angle $2\phi=0$, and a diaphragm diameter $d=0.4$ mm, while the broken-line graph corresponds to an exposure angle $\alpha = 3°$, a diffraction angle $2\phi = 0$, and a diaphragm diameter $d = 0.8$ mm;

FIG. 3a shows the variation of the diameter $2\Delta_M$ of a diffraction spot of half-brightness as a function of the distance D between the flat film and the sample with the continuous-line graph corresponding to the conditions $\alpha = 3°$, and $d = 0.4$ mm, and the broken-line graph corresponding to the conditions $\alpha = 3°$ and $d = 0.8$ mm.

Figure 3B:
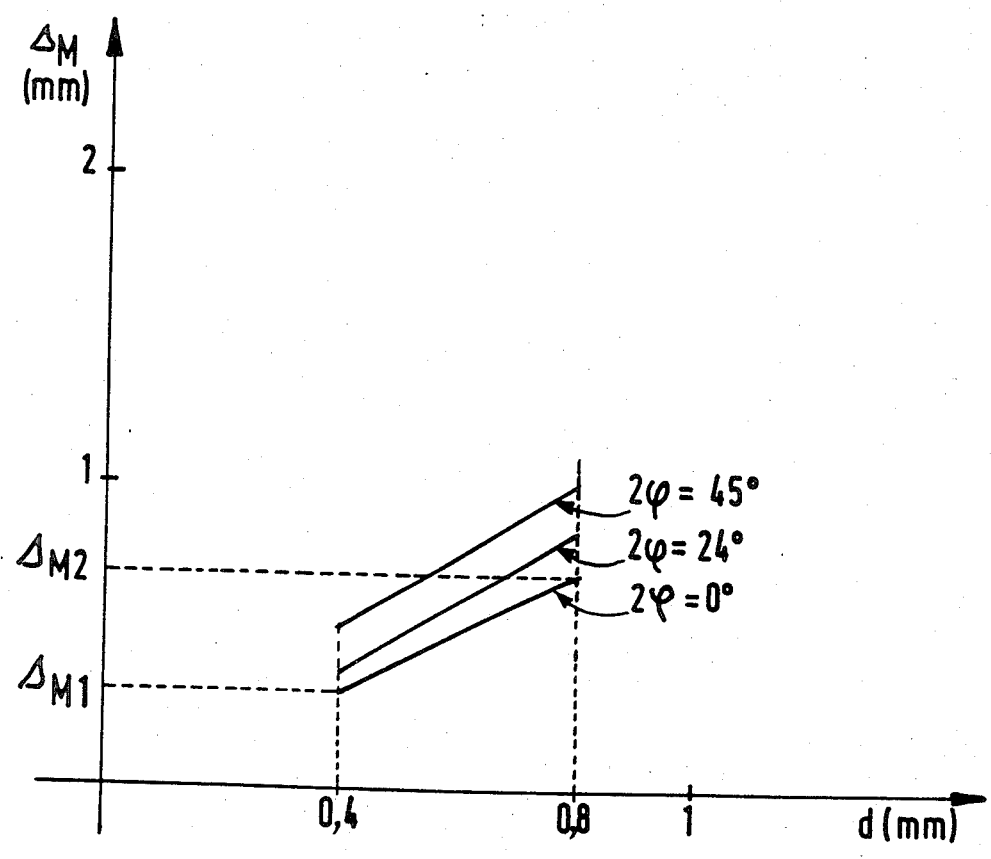

FIG. 3b represents the variation of the radius $\alpha_M$ of a diffraction spot of half-brightness as a function of the diameter d of the diaphragms under the conditions $\alpha = 3°$ and $D = 30$ mm.

Figure 1A:
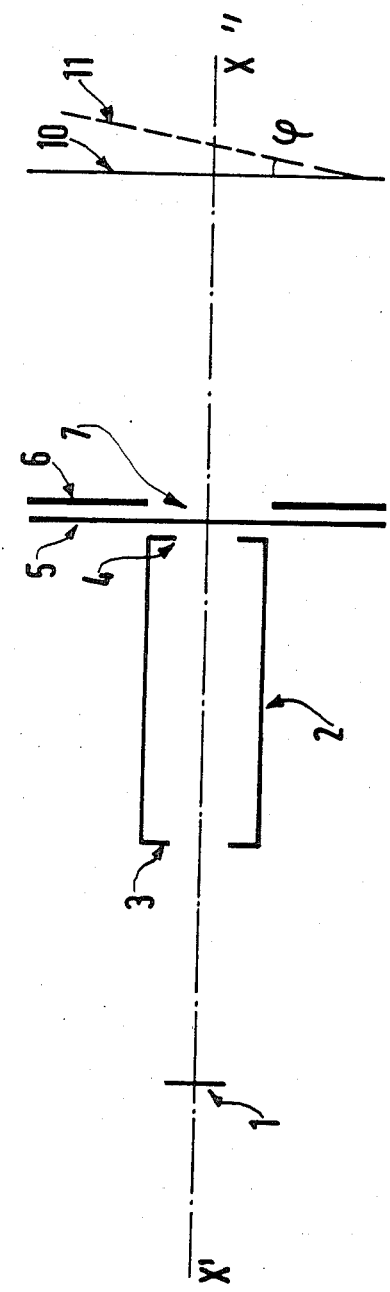
FIG. 1a shows the device in a cross-section parallel to the optical axis X'X"

As shown in cross-section in FIG. 1a, the device comprises an X-ray source 1, a collimator 2 formed by a, for example, metal tube with a diameter of several millimeters, fitted with two diaphragms 3 and 4, with an aperture d located at each extremity of the tube and, for example, removable. The device further comprises a flat film 5 mounted in a holder, which is not shown, and a transformation screen 6.

The flat-film holder, which may be a holder of the type Polaroid Ref X R7, already referred to, does not, properly speaking, form part of the invention. Any conventional flat-film magazine may be used provided it can expose both sides of the flat film since the diaphragms are formed at least partly in the transmission mode, and also provided that the front of the magazine facing the sample 10 is fitted with a transformation screen 6 if the flat film used is not very sensitive to X-rays.

If the Polaroid holder of the type referred to is used, its collimator should be removed because it is unsuitable for reasons which have been explained above. The source 1, the collimator 2, the flat-film holder and the transformation screen 6 and a sample holder for the sample 10 are mounted on a high-precision optical bench and aligned optically along an optical axis $X'X''$.

The X-ray source may, to advantage, be a Philips source of the PW2224/20 type with a tungsten anticathode, whose focus has dimensions 0.4 and 8 mm and an exposure angle $\alpha$ between 0° and 20° when exposure is effected on a point basis. These X-ray tubes are generally used at an exposure angle of at least 6° so as to obtain the greatest possible brightness with designers endeavouring to enhance the performance of the tube by increasing the distance of the anode and the size of the windows in order, precisely, to be able to use an increasingly large exposure angle.

With the present invention, such a source will be used on the contrary at an angle $\alpha$ smaller than the usual angle, namely approximately $\alpha = 3°$, so as to obtain apparent dimensions of 0.4 and 0.4 mm for the source, i.e. such that the longitudinal dimension will appear identical to the transversal direction.

Additionally, the diameter d of the diaphragms of the collimator will be chosen of the same order of magnitude, namely:

$d \approx 0.4$ mm, i.e. with a size which is half that of the diaphragm advocated in the previous state of the art.

Under these conditions the luminous intensity I of the rays which leave the source 1, pass through the collimator 2 and produce spots on the film 5, is four times smaller than in the previous state of the art, but the diffraction diagram is nevertheless of much better quality because it is of greater precision as will be shown below.

In fact, the rays leaving the edges 100 and 101 of the source 1 are limited by the edges 30 and 31 of the opening 103 in the diaphragm 3 on the one hand, and by the edges 40 and 41 of the opening 104 in the diaphragm 4 on the other.

These rays pass through the negative film 5 to form the central spot in the diffraction diagram. This spot is made up of a zone of full light delimited by the rays 20 and 21 which are parallel to the optical axis, and a penumbra zone delimited by the rays 30 and 31, which impinge on the edges 40 and 41 of the diaphragm 4.

It is certain that if the dimensions of the source increase, then the dimensions of the penumbra zone will increase enormously. It is no less certain that if only one of the dimenions of the source increases, then the penumbra zone will have its dimensions increased in that direction and will become elliptical.

That is why it is important that the source should have identical apparent dimensions both in the transversal direction and in the longitudinal direction, as is obtained for the source used as an example, with an exposure angle $\alpha = 3°$.

Figure 1B:
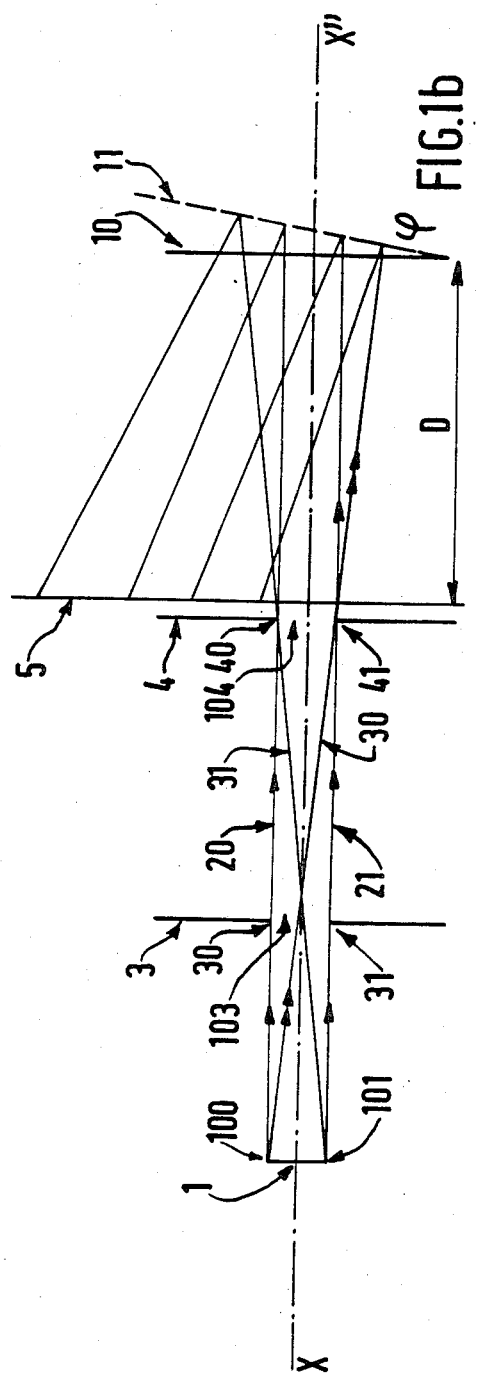
FIG. 1b shows the path of the X-rays in such a device.

As is shown in FIG. 1a, after having passed through the film 5, the rays from the source pass through the transformation screen 6 via a circular opening 7 with a diameter greater than the diameter d of diaphragm 4. Then, as is shown in FIG. 1b, the rays impinge on the sample 10 and are reflected by lattice planes such as plane 11 which forms an angle $\phi$ with the entry face of the sample.

After reflection from the lattice plane 11, the rays return to the transformation screen 6 which transforms the X-ray photons into visible photons and, in their turn, produce spots on film 5.

Upon being reflected from lattice plan 11, rays 20 and 21, parallel to the optical axis, delimit the full-light zone of a diffraction spot which is characteristic of that lattice plane, whereas the outside rays 30 and 31, which impinge on the edges of diaphragm 4, delimit the penumbra zone surrounding the full-light zone of that spot.

The diameter of the full-light zone depends only on the dimensions of the source and of the diaphragms, and does not depend on the distance D between the film and the sample. This is particularly clear from FIG. 2 which gives the distribution of the luminous intensity I as a function of the distance $\Delta$ from the center of a diffraction spot with the distance D being taken as the parameter.

On the other hand, the diameter of the penumbra zone depends on this distance D. That is why the expert will choose a reasonable distance D so as not to increase that diameter excessively.

But the diameters of both the full-light zone and the penumbra zone depend mainly on the dimensions of the source and of the diaphragms.

FIG. 2 shows that for the same exposure angle of $\alpha = 3°$ and for the same distance $D = 30$ mm, for example, the half-brightness diameter $2\Delta_{M2}$ of the diffraction spot obtained with diaphragms of a diameter $d = 0.8$ mm is more than double the diameter $2\Delta_{M1}$ of the diffraction spot obtained with diaphragms of diameter $d = 0.4$ mm.

However, the ever-increasing need for semiconductor substrates oriented with great precision is resulting in efforts to obtain increasingly exact diffraction diagrams. In effect, it is not just a matter of identifying diffraction spots but also of utilizing the tool which the diagram provides in order to succeed in orientating a single crystal so as to be able to use it as a substrate for epitaxial layers, or implanted layers, or as a seed for starting the growth of a large single crystal.

To satisfy these requirements, the half-brightness radius $\Delta_M$ of the diffraction spot must not exceed 0.5 mm.

Furthermore, it has to be borne in mind that the diffraction diagram is recorded on a negative flat film and that if insufficient luminous intensity is available, the exposure times will have to be increased, which results in a widening of the recorded spots.

That was why a large diaphragm diameter and large source dimensions were advocated in the previous state of the art.

The curves shown in FIGS. 2, 3a and 3b prove that the aim is achieved by the device according to the invention under conditions which are totally different from the conditions advocated by the previous state of the art since, while the brightness of the diffraction spots is four times smaller, the diameter of the spots is nevertheless smaller by at least half.

In general, in order to obtain diffraction spots with a radius $\Delta_M$ smaller than or equal to 0.5 mm, the diameter of the diaphragms and the apparent dimensions of the X-ray source must at most be of the same order of magnitude as this desired radius $\Delta_M$, with the sample being placed at the smallest possible distance D from the film.

FIG. 3a shows the variation of the semi-intensity dimensions of the mean diameter $2\Delta_M$ of the diffraction spots for an exposure angle $\alpha=3°$, as a function of the distance D between the film and the sample with the diffraction angle $2\phi$ being taken as the parameter. The broken-line curves corresponding to diaphragms with an opening d=0.8 mm show that spots with a diameter of less than a millimeter can never be achieved.

On the other hand, the continuous-line curves corresponding to diaphragms with an opening d=0.4 mm show that it is easy to obtain spots of suitable dimensions with the device according to the invention by placing the sample at a reasonable distance D, e.g. less than 60 mm, from the film.

FIG. 3b shows the variations of the dimensions of the half-intensity mean radius $\Delta_M$ of the diffraction spots for an exposure angle of $\alpha=3°$ and a distance D=30 mm, with the diffraction angle $2\phi$ being taken as the parameter, and with these curves being plotted for the device according to the invention (d=0.4 mm). This figure clearly shows that this mean radius $\Delta_M$ is of the order of magitude of the opening d in the diaphragms when the distance D of the sample remains reasonable.

The device according to the invention makes it possible to obtain, under the conditions stated, a precision of the order of 0.1° in the orientation of crystals, i.e. practically ten times better than in the previous state of the art.

What is claimed is:

1. A Laue camera comprising
X-ray source means for directing an X-ray beam at a sample, said X-ray source means being defined by two focal dimensions and an exposure angle to represent a focus of said X-ray source means,
wherein said exposure angle is of a value to provide two apparent focal dimensions of the same size,
holder means for holding photographic film, and
collimator means between said X-ray source means and said holder means for collimating said X-ray beam, said collimator means including two diaphragms, and said collimator means being placed adjacent said holder means,
wherein said two diaphragms having openings of a diameter equal to said two apparent focal dimensions, and wherein means for supporting said sample is provided at a surface of said film opposite to said X-ray source means.

2. A Laue camera comprising
X-ray source means for directing an X-ray beam at a sample, said X-ray source means being defined by two focal dimensions, said focal dimensions being 8×0.4 mm, and an exposure angle to represent a focus of said X-ray source means,
wherein said exposure angle is of a value of 3° to provide two apparent orthogonal focal dimensions of 0.4 and 0.4 mm,
holder means for holding photograpic film, and
collimator means between said X-ray source means and said holder means for collimating said X-ray beam, said collimator means including two diaphragms, and said collimator means being placed adjacent said holder means,
wherein said two diaphragms have openings of a diameter being 0.4 mm and equal to said two apparent focal dimensions, said diameter being smaller than an average radius for an X-ray spot in a diffraction diagram obtained from said sample, and wherein means for supporting said sample is provided at a side of said film opposite to said X-ray source means and disposed at a distance of less than 100 mm from said film.

* * * * *